United States Patent [19]

Gonzalez

[11] Patent Number: 4,508,738
[45] Date of Patent: Apr. 2, 1985

[54] NON-SUCROSE FERMENTING *PEDIOCCUS PENTOSACEUS*

[75] Inventor: Carlos F. Gonzalez, Sarasota, Fla.

[73] Assignee: Microlife Technics, Inc., Sarasota, Fla.

[21] Appl. No.: 359,164

[22] Filed: Mar. 17, 1982

[51] Int. Cl.³ .................. A23B 4/12; A23L 1/31; C12P 7/56; C12N 15/00; C12N 1/20; C12N 1/00; C12R 1/01

[52] U.S. Cl. .................. 426/55; 426/7; 426/59; 435/139; 435/172.3; 435/253; 435/317; 435/822; 935/29; 935/59

[58] Field of Search ........... 435/139, 172, 253, 317, 435/822, 172.3; 426/7, 55, 59

[56] References Cited

U.S. PATENT DOCUMENTS 4,248,513 12/1980 Satz ........................... 426/59
4,303,679 12/1981 Raccach ..................... 426/59

OTHER PUBLICATIONS

Terzaghi, Betty R., Improved Medium for *Lactic streptococci* and Their Bacterophages: Applied Microbiol. 29, 807 (1975).

LeBlanc, Donald J., Rapid Screening Procedure for Detection of Plasmids in *streptococci:* J. Bacteriol. 140, 1112 (1978).

Komatsu et al., Microbiology, D. Schlessinger (ed.), ASM Publications, Washington, D.C., 1981, pp. 384–387.

*Bergey's Manual of Determinative Bacteriology*, 8th edition, Buchanan et al. (ed.), Williams & Wilkins Co., Baltimore, 1974, p. 515.

Sakaguchi et al., in *Molecular Breeding and Genetics of Applied Microorganisms*, Sakaguchi et al. (ed.), Academic Press, New York, 1980, pp. 29–33.

Cook: J. Gen. Microbiol. 92, 49 (1976).

Palchaudhuri et al., Chem. Abstr. 87:50072s (1977) of J. Bacteriol. 130, 1402 (1977).

Wohlhieter et al., Chem. Abstr. 83:24970f (1975) of J. Bacteriol. 122, 401 (1975).

Primary Examiner—Lionel M. Shapiro
Assistant Examiner—James Martinelli
Attorney, Agent, or Firm—Ian C. McLeod

[57] ABSTRACT

Non-sucrose fermenting strains of *Pediococcus pentosaceus* are described. The non-sucrose fermenting *Pediococcus pentosaceus* strains have been cured to remove a single, natural plasmid which has been found to control the fermentation of sucrose to produce lactic acid. The natural plasmid removed is between about 30 to 35 megadaltons in molecular weight. Compositions including the non-sucrose fermenting strains of *Pediococcus pentosaceus* are useful for food fermentations, particularly meat fermentations.

23 Claims, No Drawings

NON-SUCROSE FERMENTING *PEDIOCCUS PENTOSACEUS*

BACKGROUND OF THE INVENTION

The present invention relates to non-sucrose fermenting strains of *Pediococcus pentosaceus* useful for fermenting meat. The *Pediococcus pentosaceus* strains have been cured to remove a naturally occurring plasmid such that they are no longer able to ferment sucrose to produce lactic acid.

PRIOR ART

The present invention relates to an improvement of the invention described in U.S. Pat. No. 4,303,679 to Raccach wherein *Pediococcus pentosaceus* NRRL-B-11,465 is described for meat fermentations in the presence of a stimulatory metal ion. U.S. Pat. No. 4,238,513 to Satz describes the same strain without the stimulatory metal salts.

As described in U.S. Pat. No. 4,303,679 to Raccach, the stimulatory metal ions, particularly manganese ions, with *Pediococcus pentosaceus* NRRL-B-11,465 provide a significant advantage in commercial meat fermentations. The fermentations are rapid at low temperatures which is an economic and processing advantage. One problem which has been encountered is that when there are significant amounts of sucrose in the meat formulations, because of added fillers or bulking agents, the pH of the fermented meat drops to too low a level (i.e. below pH 4.6) and the fermented meat tastes sour. This is particularly a problem with hams and sausages.

OBJECTS

It is therefore an object of the present invention to provide new strains of *Pediococcus pentosaceus* which do not have the ability to ferment sucrose. It further is an object of the present invention to provide bacterial compositions including the new strains which are stable upon storage so as to maintain a good capability for producing lactic acid and which cannot revert to having the ability to ferment sucrose as a function of time. It is further an object of the present invention to provide a plasmid curing method for producing the new strains. These and other objects will become increasingly apparent from the following description.

GENERAL DESCRIPTION

The present invention relates to strains of *Pediococcus pentosaceus* adapted for food fermentations which is unable to ferment sucrose to lactic acid as a result of the removal of a single naturally occurring plasmid from a known strain of *Pediococcus pentosaceus*. The invention further relates to an improvement in the method for preparation of fermented foods by providing a culture in the foods and then fermenting which comprises: providing in the foods a strain of a *Pediococcus pentosaceus* which is unable to ferment sucrose to lactic acid as a result of the removal of a single naturally occurring plasmid from a known strain of *Pediococcus pentosaceus*. The single plasmid which has been removed measures between about 30 to 35 megadaltons in molecular weight and has been designated as plasmid pSRQ1. The preferred new non-sucrose fermenting strain is *Pediococcus pentosaceus* NRRL-B-15007 or 15019. The non-sucrose fermenting strain can be characterized as pla$^-$ (plasmid negative) and suc$^-$ (sucrose negative).

The invention also relates to the method of removing a plasmid from a known strain of *Pediococcus pentosaceus* having the ability to ferment sucrose to lactic acid with the plasmid which comprises contacting viable known strain cells of *Pediococcus pentosaceus* with a sub-lethal, curative concentration of a plasmid curing agent or exposure to curing temperatures to remove the plasmid from the cells. The cured pla$^-$, suc$^-$ *Pediococcus pentosaceus* strains produced are adapted for the food fermentations when provided in concentrated form, preferably containing at least about $1 \times 10^6$ cells per ml.

To prepare the non-sucrose strains, a pla$^+$, suc$^+$ *Pediococcus pentosaceus* was used. The known species has at least one commercially useful strain which is pla$^+$, suc$^+$ *Pediococcus pentosaceus* NRRL-B-11,465. The strain is particularly useful at low temperatures. The pla$^+$, suc$^+$ *Pediococcus pentosaceus* was subjected to various curing agents and procedures so that the cells were not killed and various new pla$^-$, suc$^-$ *Pediococcus pentosaceus* strains were produced. Suitable curing agents are for instance ethidium bromide, acriflavin, acridine orange, and proflavin at sub-lethal levels in a liquid growth medium. Elevated temperatures alone or with the curing agents can be used to more rapidly remove plasmids as is known in the prior art. The temperatures are no higher than 50° C. which is lethal to the *Pediococcus pentosaceus* strains.

A plasmid profile was determined by lysis and agarose gel electrophoresis on the parent strain and the new strains as described in LeBlanc et al, *J. of Bacteriology* Vol 140, No. 3, pages 1112 to 1115 (1979). The absence of the plasmid from the new strain was confirmed by subjecting sodium dodecyl sulfate cleared lysates of the parent and the non-sucrose fermenting strains to cesium chloride-ethidium bromide gradients. The gradients showed that no covalently closed circular DNA was present in the non-sucrose fermenting strain while the gradient of the parent showed presence of covalently closed circular DNA. The covalently closed circular DNA from the parent strain was removed, dialyzed and subjected to Slab Agarose Gel Electrophoresis (SAGE) in parallel with known size standards. It was found that a single natural plasmid had been removed by the curing. The removed plasmid was 33.5 megadaltons in molecular weight based upon comparisons with known size standards in parallel electrophoresis patterns; however to allow for variance in size the range has been specified as 30–35 megadaltons herein.

The resulting pla$^-$, suc$^-$ *Pediococcus pentosaceus* were concentrated preferably to at least about $1 \times 10^8$ cells per ml and then used to produce pepperoni containing sucrose with and without manganese ions as described in Raccach U.S. Pat. No. 4,303,679. Preferably the non-sucrose fermenting strains were used in substantially pure form but can be mixed with other food fermenting bacteria as is known in the prior art. Various culture preservation agents can be used as is known in the prior art. Glycerol is preferred for frozen concentrates as a freezing stabilizing agent. Lyophilized bacterial concentrates can also be used. It was found that the non-sucrose fermenting strains were slightly slower than pla$^+$, suc$^+$ *Pediococcus pentosaceus* NRRL-B-11,465; however, they were still commercially useful as can be seen from the Examples.

SPECIFIC DESCRIPTION

The following example shows the steps in the isolation and use of pla⁻, suc⁻ *Pediococcus pentosaceus* NRRL-B-15,019

EXAMPLE 1

(1) Test standards

The following plating medium was used to detect the carbohydrate fermentation characteristics of an isolated strain:

(a) A Basal Sugar Medium (BSM) was used for plating of *Pediococcus pentosaceus* to show fermentation. Fermentation of sugars added to the medium is shown by color change of a purple color to yellow as a result of the lowered pH. The pH change occurs at pH 5.2.

Tryptone: 20 grams
Yeast Extract: 5 grams
Gelatin: 2.5 grams
Sodium acetate: 1.5 grams
Sodium chloride: 4.0 grams
Agar: 15 grams
0.4% Bromocresol Purple (BCP)
Water: 1000 ml After heat treatment of 15 min at 121° C., a filter-sterilized (0.22$\mu$ filter) solution of concentrated carbohydrate (20% w/v) was aseptically added to give a final concentration of 0.5% (w/v) carbohydrate in the BSM medium.

The medium was aseptically poured into Petri dishes and allowed to solidify at room temperature.

(b) Supplemental carbohydrates added to Medium (BSM) for determining sugar fermentation characteristics were:

BSM + glucose = BG
BSM + xylose = BX
BSM + melibose = B-Mel
BSM + maltose = B-Mal
BSM + lactose = BL
BSM + sucrose = BS A corresponding broth culture did not contain agar.

(c) The starting pla⁺, suc⁺ *Pediococcus pentosaceus* strains were tested against all of these carbohydrates to insure that they were active in generating acid with glucose and other carbohydrates including sucrose. As will be seen, the sucrose negative strains derived from the curing of the natural plasmid are also melibose and raffinose negative.

(d) Aerobic incubation was determined to be satisfactory to show lactic acid produced. Anaerobic conditions can be used.

(2) Curing

Steps in the isolation of pla⁻, suc⁻ *Pediococcus pentosaceus* strains:

(a) Grow the *Pediococcus pentosaceus* NRRL-B-11,465 overnight in Elliker Broth (Difco cat. no. 0974-01).

(b) Inoculate *Pediococcus pentosaceus* into tubes of the Elliker broth containing increasing concentrations of ethidium bromide (EB) or acriflavin (AF). The concentrations are preferably between about 10 and 20 micrograms per milliliter.

(c) Incubate at 32° C. (preferably between about 30° and 48° C.) in a water bath and in the dark for between about 18 and 24 hours;

(d) Read the tubes for growth as evidenced by cell turbidity in the presence of EB or AF; and (e) Plate the resulting strains which grow on BS as set forth at paragraph (1) above, to detect suc⁻ strains which do not produce lactic acid from sucrose.

The curing agents (EB and AF) remove the plasmids from the bacteria. Using this method and growing in BS medium, several suc⁻ strains were isolated. The strains also had lost the ability to ferment and produce acid from melibose and raffinose (see Table I as discussed below), thus indicating a loss of a function(s) involved in the metabolism of at least three disaccharides.

These results suggested the possible removal of a plasmid from the pla⁺, suc⁺ *Pediococcus pentosaceus* NRRL-B-11,465. This surmise was subsequently confirmed by agarose gel electrophoresis patterns using the LeBlanc et al procedure.

Pla⁻, suc⁻ *Pediococcus pentosaceus* NRRL-B-15019 was selected for testing. The carbohydrate fermentation pattern (using BBL Minitek ® system) of NRRL-B-15109 is shown in Table I by comparison to the parent strain NRRL-B-11,465 as described in U.S. Pat. No. 4,303,679 to Raccach and 4.238,513 to Satz.

TABLE I

| | REACTION | | NRRL-B- | |
|---|---|---|---|---|
| SUBSTRATE | POSITIVE | NEGATIVE | 11,465 | NRRL-B- |
| Adonitol | yellow to yellow orange | Red orange | − | − |
| Arabinose | yellow to yellow orange | Red orange | + | + |
| Cellobiose | yellow to yellow orange | Red orange | + | + |
| Dextrose | yellow to yellow orange | Red orange | + | + |
| Dulcitol | yellow to yellow orange | Red orange | − | − |
| Galactose | yellow to yellow orange | Red orange | + | + |
| Glycerol | yellow to yellow orange | Red orange | ∓ | ∓ |
| Inositol | yellow to yellow orange | Red orange | − | − |
| Lactose | yellow to yellow orange | Red orange | + | + |
| Maltose | yellow to yellow orange | Red orange | + | + |
| Mannitol | yellow to yellow orange | Red orange | − | − |
| Mannose | yellow to yellow orange | Red orange | + | + |
| Melibiose | yellow to yellow orange | Red orange | + | − |
| Nitrate reductase | dark rust-red | Yellow, white or pink | − | − |
| ONPG | light yellow | White | − | − |
| Raffinose | yellow to yellow orange | Red orange | + | − |
| Rhamnose | yellow to yellow orange | Red orange | ± | − |
| Salicin | yellow to yellow orange | Red orange | ± | ± |
| Sorbitol | yellow to yellow orange | Red orange | − | − |
| Sucrose | yellow to yellow orange | Red orange | + | − |
| Trehalose | yellow to yellow orange | Red orange | + | + |
| Xylose | yellow to yellow orange | Red orange | − | − |
| Starch | yellow to yellow orange | Red orange | − | − |
| Esculin | brown | Off white | + | + |

TABLE I-continued

| SUBSTRATE | REACTION POSITIVE | NEGATIVE | NRRL-B-11,465 | NRRL-B- |
|---|---|---|---|---|
| Lysine | yellow | | + | + |
| Argonine | yellow | | + | + |

Clearly, the new pla⁻, suc⁻ is different from its parent.

(3) Bacterial Concentrates

Bacterial concentrates of NRRL-B-11,465 and NRRL-B-15,019 were prepared as described in U.S. Pat. No. 4,303,679 to Raccach. The cells were grown in the following medium:

Yeast extract: 210 grams
Dextrose: 500 grams
Corn steep: 500 grams
Magnesium sulfate: 0.264 grams
Manganese sulfate: 0.264 grams
Ferric sulfate: 0.1264 grams
Water to 10 liters.

The pH was adjusted to 6.8 with ammonia. The pH was maintained at about 6.0 with continuous pH adjustment during growth by adding ammonia. The cells were concentrated by centrifugation and the pellet was resuspended with supernatant medium to 1/10 of the original volume and glycerin was added to a final concentration of 10% (w/w). (18.4 g of 36.9% (w/v) solution to 100 grams of concentrate) was added to some of the concentrates. The concentrates were frozen for storage prior to use and were found to be storage stable. The concentrates contained about $2 \times 10^{11}$ cells per ml.

(4) Sausage Preparation

Pepperoni sausage was made using pla⁻, suc⁻ *Pediococcus pentosaceus* NRRL-B-15,019 and NRRL-B-11,465. The meat formulation was 3813.6 grams of pork plus 1634.4 grams of beef coarsely chopped to which was added:

Salt 179.78 grams total (3.3%) by weight including:
BHA: 1.64 ml of 10% soln (10% w/v); (0.003%)
BHT: 1.64 ml of 10% soln (10% w/v); (0.003%)
Sodium citrate: 1.64 ml of 10% soln (10% w/v); (0.003%)
Dextrose: 39.48 g
Spices: 30.60 g
Sodium nitrite: 4.2 ml (200 mg/ml water solution)

The concentrate was added at about $4 \times 10^7$ cells per gram of meat formulation. The manganese ion was present in the amount of about 4 ppm in the meat formulation. The results are shown in Table II.

TABLE II

| | pla⁺, suc⁺ | | pla⁻, suc⁻ | |
|---|---|---|---|---|
| Hours | NRRL-B-11,465 | Control-NRRL-B-11,465 + Mn | NRRL-B-15,019 | NRRL-B-15,019 + Mn |
| 8.5 | 5.54 | 5.19 | 5.45 | 5.38 |
| 10.0 | 5.52 | 5.01 | 5.44 | 5.18 |
| 11.0 | 5.42 | 4.78 | 5.44 | 5.04 |
| 12.5 | 5.35 | 4.63 | 5.37 | 4.90 |
| 14.0 | 5.30 | — | 5.33 | 4.86 |
| 15.75 | 5.26 | — | 5.28 | 4.81 |

The internal meat temperature was 35° C. (95° F.) after 9 hours.

The result, as can be seen from Table II, is that the pla⁻, suc⁻ NRRL-B-15,019 performed almost as well as pla⁺, suc⁺, NRRL-B-11,465 and yet does not ferment sucrose. Organoleptically the NRRL-B-15,019 pepperoni sausage was indistinguishable from that made with NRRL-B-11,465 and the color was comparable.

An attempt was made to isolate a faster pla⁻, suc⁻ sausage making strain using a different procedure from that described in Example I. *Pediococcus pentosaceus* NRRL-B-11,465 was subjected to elevated temperature curing conditions for removal of the plasmid.

EXAMPLE 2

Curing of *Pediococcus pentosaceus* NRRL-B-11,465 was performed at 32° C., 42° C., 45° C. and 48° C. without a curing agent in BG broth without agar.

(1) Test standards.

The plating medium used to detect the carbohydrate fermentation characteristics of an isolated strain was the same as BSM of Example I except that 19 g of β-glycerophosphate sodium salt were added to 1000 ml BSM prior to steam sterilization. This medium was designated as PM. β-glycerophosphate was added as buffering agent to enable easier detection of non-carbohydrate (specific) fermenting colonies in the presence of large numbers of carbohydrate (specific) fermenting colonies.

(2) Curing

Steps in the isolation of pla⁻, suc⁻ *Pediococcus pentosaceus* strains:

(a) Grow the *Pediococcus pentosaceus* NRRL-B-11,465 (pla⁺, suc⁺) overnight in BG broth of Example 1 (without agar).

(b) Inoculate *Pediococcus pentosaceus* into tubes of BG broth and incubate in water baths set at 32° C., 42° C., 45° C. and 48° C. respectively for 18 hours;

(c) Read the tubes for cell turbidity; and (d) Plate the resulting strains which grow on BS agar, i.e. BSM plus sucrose, (0.5% w/v) and agar) to detect suc⁻ strains which do not produce lactic acid from sucrose. The rates at which non-sucrose isolates were obtained by each temperature treatment are contained in Table III.

TABLE III

| TEMPERATURE | TOTAL COLONIES TESTED | SUC⁻ COLONIES | CURING RATE (%) |
|---|---|---|---|
| 32° C. | 1866 | 10 | 0.53% |
| 42° C. | 1389 | 7 | 0.50% |
| 45° C. | 538 | 4 | 0.74% |
| 48° C. | 499 | 8 | 1.60% |

*Pediococcus pentosaceus* NRRL-B-15007 was selected from BS agar and was tested for ability to ferment various carbohydrates using the BBL Minitek ® system. The carbohydrate fermentation pattern of *Pediococcus pentosaceus* NRRL-B-15007 is shown in Table IV by comparison to the parent strain NRRL-B-11,465 as described in U.S. Pat. No. 4,303,679 to Raccach and No. 4,238,513 to Satz and to strains NRRL-B-15,019 of Example I. In addition to sucrose, *Pediococcus pentosaceus* NRRL-B-15007 also had lost the ability to ferment and produce acid from melibose and raffinose (see Table IV), thus indicating a loss of function involved in the metabolism of at least three disaccharides. These results suggest the possible removal of a plasmid from the pla+, suc+ *Pediococcus pentosaceus* NRRL-B-11,465. This surmise was subsequently confirmed by agarose gel electrophoresis patterns using the LeBlanc et al procedure. Clearly, the new pla−, suc− *Pediococcus pentosaceus* NRRL-B-15007 is different from its parent. It appears to be very similar to the strain of Example 1.

was provided. A manganese sulfate solution was used to provide about 4 ppm of manganese ion in the meat.

The sausage was stuffed into casings and was incubated at 35° C. internal meat temperature.

RESULTS

At 0 hours the pH was 5.74. The internal meat temperature at 9 hours was 35° C.

TABLE IV

| SUBSTRATE | REACTION POSITIVE | REACTION NEGATIVE | NRRL-B-11,465 | NRRL-B-15,019 | NRRL-B-15007 |
|---|---|---|---|---|---|
| Adonitol | yel to yel orange | Red orange | − | − | − |
| Arabinose | yel to yel orange | Red orange | + | + | + |
| Cellobiose | yel to yel orange | Red orange | + | + | + |
| Dextrose | yel to yel orange | Red orange | + | + | + |
| Dulcitol | yel to yel orange | Red orange | − | − | − |
| Galactose | yel to yel orange | Red orange | + | + | + |
| Glycerol | yel to yel orange | Red orange | ∓ | ∓ | ∓ |
| Inositol | yel to yel orange | Red orange | − | − | − |
| Lactose | yel to yel orange | Red orange | + | + | + |
| Maltose | yel to yel orange | Red orange | + | + | + |
| Mannitol | yel to yel orange | Red orange | − | − | − |
| Mannose | yel to yel orange | Red orange | + | + | + |
| Melibiose | yel to yel orange | Red orange | + | − | − |
| Nitrate reductase | dark rust-red | Yellow, white or pink | − | − | − |
| ONPG | light yellow | White | − | − | − |
| Raffinose | yel to yel orange | Red orange | + | − | − |
| Rhamnose | yel to yel orange | Red orange | ± | − | − |
| Salicin | yel to yel orange | Red orange | ± | ± | ± |
| Sorbitol | yel to yel orange | Red orange | − | − | − |
| Sucrose | yel to yel orange | Red orange | + | − | − |
| Trehalose | yel to yel orange | Red orange | + | + | + |
| Xylose | yel to yel orange | Red orange | − | − | − |
| Starch | yel to yel orange | Red orange | − | − | − |
| Esculin | brown | Off white | + | + | + |
| Lysine | yellow | | + | + | + |
| Argonine | yellow | | + | + | + |

The strain was concentrated and frozen with or without manganese ion as in Example 1. The concentrate contained $2 \times 10^{11}$ cells per ml.

The NRRL-B-15007 and NRRL-B-11,465 were used to make sausage pepperoni using 2542.4 grams of chopped pork and 1089.6 grams of chopped beef with 119.86 grams (3.3% by weight) of salt including:

BHA: 1.1 ml of 10% soln (w/v)
BHT: 1.1 ml of 10% soln (w/v)
Sodium citrate: 1.1 ml of 10% soln (w/v)
Dextrose: 36.32 g
Spice: 20.4 g
Sodium nitrite: 2.80 g (200 mg/ml water solution)

The mixture was divided into four (4) aliquots of 2 pounds each and evaluated as follows:

(a) Control 1. The concentrate of NRRL-B-11,465 (contained $1 \times 10^{11}$ cells per ml) was diluted with water so as to provide $2 \times 10^7$ cells per gram of the meat formulation.

(b) Control 2. The concentrate of NRRL-B-11,465 was diluted so as to provide $2 \times 10^7$ cells per gram of the meat formulation. A solution of manganese sulfate monohydrate was used to provide about 4 ppm manganese ion in the meat formulation.

(c) A concentrate of NRRL-B-15007 was used having a viable cell count of $2.0 \times 10^{11}$ cells per ml. The concentrate was diluted with water so as to provide $2 \times 10^7$ cells per gram of the meat formulation.

(d) A concentrate of NRRL-B-15007 was used with added manganese sulfate. The concentrate was diluted so that $2 \times 10^7$ cells per gram of the meat formulation

| Hours | (a) | (b) | (c) | (d) |
|---|---|---|---|---|
| 8.5 | 5.38 | 5.32 | 5.62 | 5.41 |
| 9.5 | 5.35 | 5.11 | 5.53 | 5.29 |
| 10.5 | 5.25 | 4.83 | 5.48 | 5.15 |
| 11.5 | 5.20 | 4.69 | 5.42 | 5.02 |
| 12.5 | — | — | — | 4.90 |

It was found that:

(1) Pla−, suc− NRRL-B-15007 when not stimulated with manganese is approximately 2 hours slower than parent pla+, suc+ NRRL-B-11,465.

(2) Pla−, suc− NRRL-B-15007 is not stimulated by manganese to same extent as pla+, suc+ NRRL-B-11,465.

(3) Pla−, suc− NRRL-B-15007 when stimulated by manganese is approximately 2 hours slower than pla+, suc+ NRRL-B-11,465 stimulated with Mn.

(4) The sausage was excellent and had good color. The slightly slower fermentation time did not affect the commercial use of pla−, suc− NRRL-B-15007.

The strain NRRL-B-15007 was comparable to that of Example 1 and was not appreciably faster in food fermentation. It appeared that the removal of the plasmid produced a slowing of the meat fermentation activity of the pla−, suc− strains.

I claim:

1. A storage stable biologically pure strain of *Pediococcus pentosaceus* adapted for food fermentations which strain is unable to ferment sucrose to lactic acid as a result of curing removal of a single naturally occurring plasmid from a known strain of *Pediococcus pen-* tosaceus, wherein the single plasmid removed corresponds in size and in control of sucrose fermentation to a single plasmid in *Pediococcus pentosaceus* NRRL-B-11,465, and which strain with the plasmid removed is able to ferment dextrose to lactic acid in a food.

2. The strain of claim 1 as a composition containing at least about $10^6$ cells per ml.

3. The strain of claim 1 wherein the known strain from which the plasmid is removed is *Pediococcus pentosaceus* NRRL-B-11,465.

4. A composition which comprises a biologically pure culture of a *Pediococcus pentosaceus* which culture is unable to ferment sucrose to lactic acid as a result of curing removal of a naturally occurring plasmid measuring about 30 to 35 megadaltons in molecular weight from a known strain of *Pediococcus pentosaceus* containing only this plasmid, wherein the single plasmid removed corresponds in size and in control of sucrose fermentation to a single plasmid in *Pediococcus pentosaceus* NRRL-B-11,465, and which culture is able to ferment dextrose to lactic acid in a food.

5. A composition which comprises a biologically pure culture of a *Pediococcus pentosaceus* which culture is unable to ferment sucrose to lactic acid as a result of curing removal of a naturally occurring plasmid measuring between about 30 to 35 megadaltons from a known strain of *Pediococcus pentosaceus* containing only this plasmid, wherein the single plasmid removed corresponds in size and in control of sucrose fermentation to a single plasmid in *Pediococcus pentosaceus* NRRL-B-11,465, and which culture is able to ferment dextrose to lactic acid in a food and a preservation agent for the culture.

6. The composition of claim 5 wherein the preservation agent is a freezing stabilizing agent which maintains viable cells and wherein the composition is frozen.

7. The strain of claim 1 which is *Pediococcus pentosaceus* NRRL-B-15007 or NRRL-B-15019.

8. In the method for preparation of fermented foods by providing a culture in the foods and then fermenting the foods the improvement which comprises: providing in the foods a strain of *Pediococcus pentosaceus* which is unable to ferment sucrose to lactic acid as a result of curing removal of a single naturally occurring plasmid from a known strain of *Pediococcus pentosaceus*, wherein the single plasmid removed corresponds in size and in control of sucrose fermentation to a single plasmid in *Pediococcus pentosaceus* NRRL-B-11,465, wherein the fermentation is conducted in the presence of dextrose which is fermented to produce lactic acid which lowers pH of the food.

9. The method of claim 8 wherein the *Pediococcus pentosaceus* provided in the food is NRRL-B-15007 and wherein the food is a fermented meat.

10. The method of claim 8 wherein the culture provided in the food is a biologically pure strain of *Pediococcus pentosaceus* which does not ferment sucrose.

11. The method of claim 8 wherein the *Pediococcus pentosaceus* which is unable to ferment sucrose to lactic acid has been cured to remove the plasmid by contact with a sub-lethal concentration of a curing agent or at curing temperature or a combination thereof, separation of non-sucrose fermenting strains and concentration of the strains prior to providing the strain in the food.

12. The method of claim 11 wherein the curing agent is acridine orange, ethidium bromide, acriflavin or proflavin.

13. The method of claim 11 wherein the curing is at elevated temperatures no higher than 50° C.

14. A method of removing a single plasmid from a known strain of *Pediococcus pentosaceus* having the ability to ferment sucrose to lactic acid with the plasmid which comprises contacting viable known strain cells of *Pediococcus pentosaceus* with a sub-lethal curative concentration of a plasmid curing agent or exposure to curing temperatures wherein the single plasmid removed corresponds in size and in control of sucrose fermentation to a single plasmid in *Pediococcus pentosaceus* NRRL-B-11,465 and the strain with the plasmid removed is unable to ferment sucrose to lactic acid but is able to ferment dextrose to lactic acid in a food.

15. The method of claim 14 wherein the curing agent is acridine orange, ethidium bromide, acriflavin or proflavin.

16. The method of claim 14 wherein *Pediococcus pentosaceus* NRRL-B-15007 or NRRL-B-15019 is produced without the plasmid.

17. The method of claim 14 wherein the curing is at elevated temperatures no higher than 50° C.

18. The method of claim 8 wherein the known strain from which the plasmid is removed is *Pediococcus pentosaceus* NRRL-B-11465.

19. The method of claim 18 wherein removal of the plasmid produces a strain which has the fermentation characteristics of *Pediococcus pentosaceus* NRRL-B-15007 or NRRL-B-15019.

20. The composition of claim 4 in admixture with a metal ion which stimulates growth of the modified strain.

21. The composition of claim 20 wherein the metal ion is manganese ion.

22. The method of claim 8 wherein the strain which is unable to ferment sucrose is in admixture with a metal ion which stimulates the growth of the modified strain.

23. The method of claim 22 wherein the metal ion is a manganese ion.

* * * * *